(12) United States Patent
Star-Lack et al.

(10) Patent No.: US 9,330,458 B2
(45) Date of Patent: May 3, 2016

(54) METHODS AND SYSTEMS FOR ESTIMATING SCATTER

(71) Applicant: VARIAN MEDICAL SYSTEMS, INC., Palo Alto, CA (US)

(72) Inventors: Josh Star-Lack, Palo Alto, CA (US); Mingshan Sun, Menlo Park, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

(21) Appl. No.: 14/409,481

(22) PCT Filed: Jun. 22, 2013

(86) PCT No.: PCT/US2013/047199
§ 371 (c)(1),
(2) Date: Dec. 19, 2014

(87) PCT Pub. No.: WO2013/192600
PCT Pub. Date: Dec. 27, 2013

(65) Prior Publication Data
US 2015/0170359 A1    Jun. 18, 2015

Related U.S. Application Data

(60) Provisional application No. 61/663,494, filed on Jun. 22, 2012.

(51) Int. Cl.
*G06K 9/00* (2006.01)
*G06T 7/00* (2006.01)
(Continued)

(52) U.S. Cl.
CPC .............. *G06T 7/0012* (2013.01); *A61B 6/032* (2013.01); *A61B 6/5282* (2013.01); *G06T 11/005* (2013.01); *G06T 2207/10081* (2013.01); *G06T 2207/30004* (2013.01)

(58) Field of Classification Search
CPC ........ G01T 1/249; G06T 11/005; G06T 7/0012
USPC .................................................. 382/128, 131
See application file for complete search history.

(56) References Cited

U.S. PATENT DOCUMENTS 5,666,391 A    9/1997  Ohnesorge et al.
6,490,476 B1 * 12/2002  Townsend et al. ............ 600/427
(Continued)

OTHER PUBLICATIONS

International Search Report and Written Opinion of the International Searching Authority, International application No. PCT/US2013/047199, Nov. 12, 2013.
(Continued)

*Primary Examiner* — Tom Y Lu
(74) *Attorney, Agent, or Firm* — SU IP Consulting

(57) ABSTRACT

Techniques described herein generally relate to estimating scatter. In one embodiment, one example method for estimating scatter associated with a target object may include generating a set of original projections associated with the target object, generating a set of reference scatter data associated with the target object at one or more selected projection angles, generating a first set of estimated scatter data associated with the target object also at the one or more selected projection angles, adjusting first values for one or more kernel parameters of one or more kernels that reduce a difference between the set of reference scatter data and the first set of estimated scatter data, interpolating the adjusted first values for remaining projections out of the set of original projections to generate second values for the one or more kernel parameters, and generating a second set of estimated scatter data associated with the target object.

20 Claims, 11 Drawing Sheets

(51) Int. Cl.
    *A61B 6/03*    (2006.01)
    *A61B 6/00*    (2006.01)
    *G06T 11/00*   (2006.01)

(56) References Cited

U.S. PATENT DOCUMENTS

| | | | |
|---|---|---|---|
| 6,687,326 B1 | 2/2004 | Bechwati et al. | |
| 7,336,760 B2 | 2/2008 | Virshup et al. | |
| 8,199,873 B2 | 6/2012 | Star-Lack et al. | |
| 8,326,011 B2 | 12/2012 | Star-Lack et al. | |
| 8,682,055 B2 | 3/2014 | Star-Lack et al. | |
| 8,705,827 B2 * | 4/2014 | Zhu et al. | 382/131 |
| 8,989,469 B2 * | 3/2015 | Fahimian et al. | 382/131 |
| 2002/0048339 A1 | 4/2002 | Schneider et al. | |
| 2003/0147491 A1 | 8/2003 | Gonzalez Trotter et al. | |
| 2003/0215057 A1 | 11/2003 | Trotter et al. | |
| 2004/0190679 A1 | 9/2004 | Waggener et al. | |
| 2007/0189440 A1 | 8/2007 | Rinkel et al. | |
| 2008/0013693 A1 | 1/2008 | Kusch et al. | |
| 2008/0253515 A1 | 10/2008 | Bertram et al. | |
| 2008/0304620 A1 | 12/2008 | Karellas | |
| 2009/0202127 A1 | 8/2009 | Bertram et al. | |
| 2009/0290682 A1 | 11/2009 | Star-Lack et al. | |
| 2010/0046696 A1 | 2/2010 | Maltz | |
| 2011/0255655 A1 | 10/2011 | Star-Lack et al. | |
| 2011/0255656 A1 | 10/2011 | Star-Lack et al. | |
| 2012/0314921 A1 | 12/2012 | Star-Lack et al. | |

OTHER PUBLICATIONS

Atila Ersahin et al., "A Digital Filtration Technique for Scatter-Glare Correction Based on Thickness Estimation", IEEE Transactions on Medical Imaging, Sep. 1995, pp. 587-595, vol. 14, No. 3.

L Alan Love et al., "Scatter Estimation for a Digital Radiographic System Using Convolution Filtering", Med. Phys., Mar./Apr. 1987, pp. 178-185, vol. 14, No. 2.

J Maltz et al., "Unified Algorithm for KV and MV Scatter and Beam-Hardening Correction Using the Convolution-Superposition Method", Medical Physics, Jun. 2006, Vo. 33, No. 6, p. 2280.

B. Ohnesorge et al., "Efficient Object Scatter Correction Algorithm for Third and Fourth Generation CT Scanners", European Radiology, 1999, pp. 563-569, vol. 9.

J.H. Siewerdsen et al., "Cone-Beam Computed Tomography with a Flat-Panel Imager: Magnitude and Effects of X-Ray Scatter", Medical Physics, Feb. 2001, vol. 28, No. 2, pp. 220-231.

J.H. Siewerdsen et al., "A Simple, Direct Method for X-Ray Scatter Estimation and Correction in Digital Radiography and Cone-Beam CT", Medical Physics, Jan. 2006, vol. 33, No. 1, pp. 187-197.

Roland E. Suri et al., "Comparison of Scatter Correction Methods for CBCT", Proceedings of SPIE, 2006, vol. 6142, pp. 614238-1-614238-10.

G. Virshup et al., "Scatter Characterization in Cone-Beam CT Systems with Offset Flat Panel Imagers", Medical Physics, Jun. 2006, vol. 33, No. 6, p. 2288.

M. Zellerhoff et al., "Low Contrast 3D-Reconstruction from C-Arm Data", Proceedings of SPIE, 2005, vol. 5745, pp. 646-655.

Lei Zhu et al., "Scatter Correction Method for X-Ray CT Using Primary Modulation: Theory and Preliminary Results", IEEE Transactions on Medical Imaging, 2006, vol. 25, No. 12, pp. 1573-1587.

Schmidtlein et al., "Validation of Gate Monte Carlo Simulations of the GE Advance/ Discovery LS PET Scanners", 2006, Medical Physics, pp. 198-208, vol. 33, No. 1.

Reitz, Development and Evaluation of a Method for Scatter Correction in KV Cone Beam Computer Tomography, Apr. 30, 2008, Doctoral Dissertation, Ruperto-Carola University of Heidelberg, Germany.

Atherton et al., "CT Doses in Cylindrical Phantoms", Physics in Medicine and Biology, 1995, pp. 891-911, vol. 40.

Jarry et al., "A Monte Carlo-based Method to Estimate Radiation Dose from Spiral CT: from Phantom Testing to Patient-Specific Models", Physics in Medicine and Biology, 2003, pp. 2645-2663.

Josh Star-Lack et al., "Scatter Correction for the On-Board Imager Using a Kernel Model", Medical Physics, Jun. 2007, p. 2342, vol. 34, No. 6, Abstract No. SU-FF-I-19.

Josh Star-Lack et al., "Efficient Scatter Correction Using Asymmetric Kernels", Medical Imaging 2009, Proceeding of SPIE, Feb. 9, 2009, pp. 1Z-1 to 1Z-12, vol. 7258.

* cited by examiner

Before

After

Before

After

Before

After

Before

After

Before

After

Before

After

Before

After

Before

After

METHODS AND SYSTEMS FOR ESTIMATING SCATTER

CROSS REFERENCE TO RELATED APPLICATION

This present application is a 371 application of International Application PCT/US2013/047199, filed Jun. 22, 2013 and entitled "METHODS AND SYSTEMS FOR ESTIMATING SCATTER." The International Application claims the benefit of the U.S. Provisional Application No. 61/663,494, filed Jun. 22, 2012. This International Application is also related to the commonly owned U.S. patent application Ser. No. 13/485,953, filed Jun. 1, 2012. The provisional application, U.S. patent application Ser. No. 13/485,953, and International Application, including any appendices or attachments thereof, are hereby incorporated by reference in their entirety.

BACKGROUND

Unless otherwise indicated herein, the approaches described in this section are not prior art to the claims in this application and are not admitted to be prior art by inclusion in this section.

Computerized tomography (CT) involves the imaging of the internal structure of a target object by collecting several projection images ("radiographic projections") in a single scan operation ("scan"), and is widely used in the medical field to view the internal structure of selected portions of the human body. In an ideal imaging system, rays of radiation travel along respective straight-line transmission paths from the radiation source, through a target object, and then to respective pixel detectors of the imaging system without generating scattered rays. However, in real systems, when a quantum of radiation is absorbed by a portion of the target object, one or more scattered rays are often generated that deviate from the transmission path of the incident radiation. These scattered rays are often received by "surrounding" detector elements that are not located on the transmission path that the initial quantum of radiation was transmitted on, thereby creating measurement errors.

The measurement errors created by scattered radiation cause artifacts and loss of spatial and contrast resolution in the radiographic projection data and the CT images produced by the imaging system. The scattered radiation can also cause numerical errors in image reconstruction algorithms. All of the foregoing leads to image degradation.

Solutions have been proposed to estimate and/or correct scattered radiation using kernel methods. In one example solution, U.S. patent application Ser. No. 12/125,053 discloses symmetric and asymmetric kernel models, which is hereby incorporated by reference in its entirety. In other example solutions, U.S. Pat. No. 8,199,873, issued on Jun. 12, 2012, and U.S. patent application Ser. No. 13/485,953, filed on Jun. 1, 2012, discloses hybrid kernel models. Due to the limitations in the scatter estimation models employed in these solutions, approximately +/−50 Hounsfield Units (HUs) uncertainties still exist for challenging situations such as pelvis scans.

Accordingly, there is a need to develop techniques that can further improve the estimation accuracy but in an efficient manner.

SUMMARY

In accordance with at least some embodiments of the present disclosure, a method for estimating scatter associated with a target object is disclosed. The method includes generating a set of original projections associated with the target object, generating a set of reference scatter data associated with the target object at one or more selected projection angles, generating a first set of estimated scatter data associated with the target object by applying one or more kernels with first values for one or more kernel parameters to a first subset of projections out of the set of original projections at the one or more selected projection angles, adjusting first values for one or more kernel parameters of the one or more kernels that reduce a difference between the set of reference scatter data and the first set of estimated scatter data, interpolating the adjusted first values for remaining projections out of the set of original projections to generate second values for the one or more kernel parameters, and generating a second set of estimated scatter data associated with the target object by applying the one or more kernels with the adjusted first values and the second values for the one or more kernel parameters.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
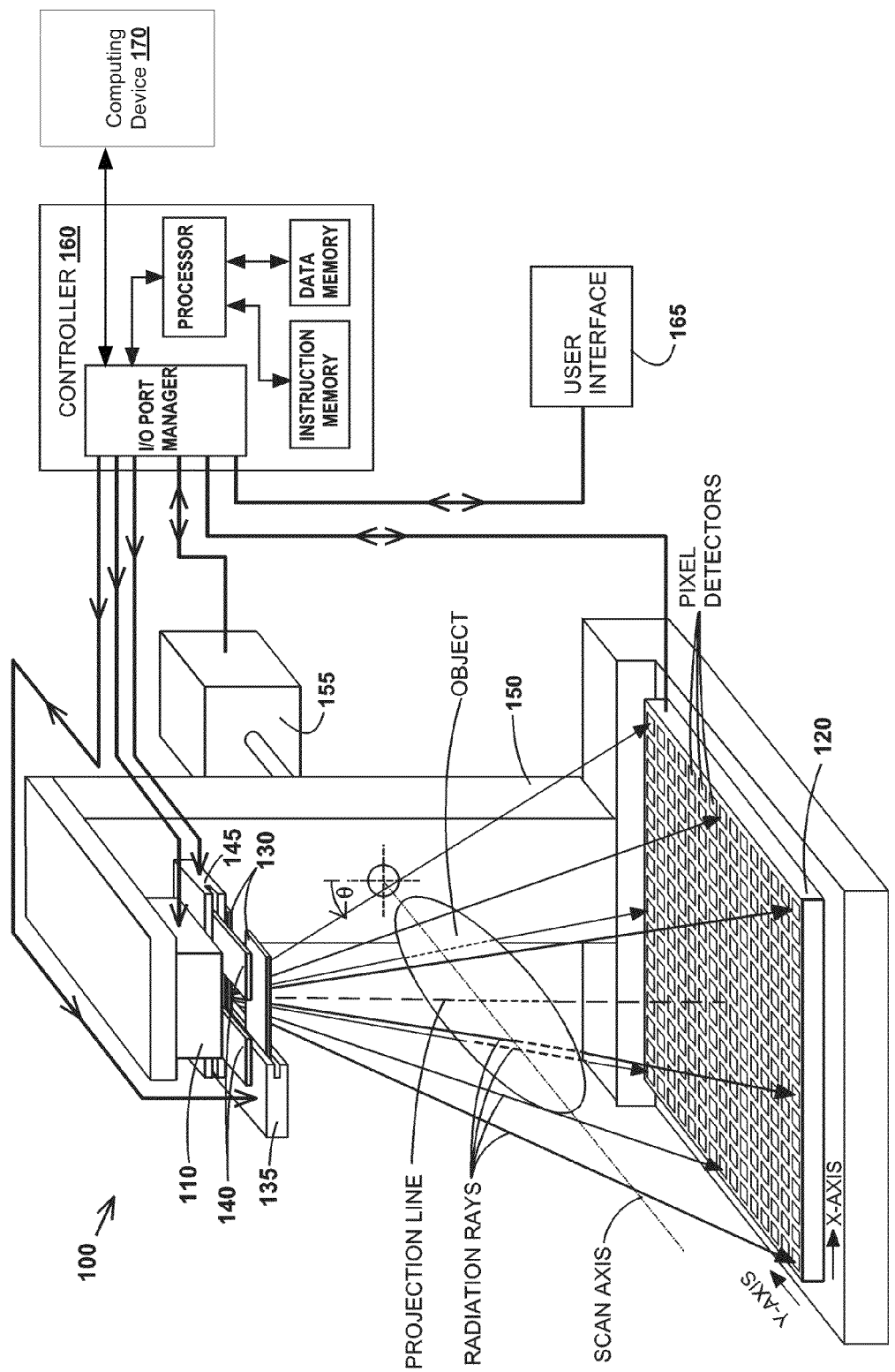
FIG. 1 is an example imaging system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Throughout the present disclosure, the terms "projection view," "projection," and "projection data" are used interchangeably.

FIG. 1 is an example imaging system 100, in accordance with at least some embodiments of the present disclosure. The imaging system 100 includes a radiation source 110, a detector 120 having pixel detectors disposed opposite to the radiation source 110 along a projection line, a first set of fan blades 130 disposed between the radiation source 110 and the detector 120, a first fan-blade drive 135 that holds the fan blades 130 and sets their positions. The edges of the fan blades 130 may be oriented substantially perpendicular to the scan axis (defined below), and are substantially parallel with the transaxial dimension (defined below) of the detector 120. As an option, the imaging system 100 may further include a second set of fan blades 140 disposed between the radiation source 110 and the detector 120, and a second fan-blade drive 145 that holds the fan blades 140 and sets their positions. The edges of the fan blades 140 may be oriented substantially parallel with the scan axis (defined below), and are substantially perpendicular to the axial dimension (defined below) of the detector 120. The fan blades are generally disposed closer to the radiation source 110 than the detector 120. They are normally kept wide open to enable the full extent of the detector 120 to be exposed to radiation, but may be partially closed in certain situations.

The imaging system 100 further includes a gantry 150 that holds at least the radiation source 110, the detector 120, and the fan-blade drives 135 and 145 in fixed or known spatial relationships to one another, a mechanical drive 155 that rotates the gantry 150 about a target object disposed between the radiation source 110 and the detector 120, with the target object being disposed between the fan blades 130 and 140 on the one hand, and the detector 120 on the other hand. The term gantry has a broad meaning, and covers all configurations of one or more structural members that can hold the above-identified components in fixed or known (but possibly movable) spatial relationships. For the sake of visual simplicity in the figure, the gantry housing, gantry support, and fan-blade support are not shown.

Additionally, the imaging system 100 further includes a controller 160, a user interface 165, and a computing device 170. The controller 160 may be electrically coupled to the radiation source 110, the mechanical drive 155, the fan-blade drives 135 and 145, the detector 120, and the user interface 165. The user interface 165 may be configured to enable a user to at least initiate a scan of the target object, and to collect measured projection data from the detector 120. The user interface 165 may be configured to present graphic representations of the measured data. The computing device 170, coupled to the controller 160, may be configured to perform simulation operations, data processing operations, and other operations.

In the imaging system 100, the gantry 150 may be configured to rotate about the target object during a scan such that the radiation source 110, the fan blades 130 and 140, the fan-blade drives 135 and 145, and the detector 120 circle around the target object. More specifically, the gantry 150 may rotate these components about a scan axis, as shown in FIG. 1, where the scan axis intersects the projection line, and is typically perpendicular to the projection line. The target object is aligned in a substantially fixed relationship to the scan axis. The construction provides a relative rotation between the projection line on the one hand and the scan axis and a target object aligned thereto on the other hand, with the relative rotation being measured by an angular displacement value $\theta$. The mechanical drive 155 may be coupled to the gantry 150 to provide rotation upon command by the controller 160. The array of pixel detectors on the detector 120 may be periodically read to obtain the data of the radiographic projections. The detector 120 has an X-axis and a Y-axis, which are perpendicular to each other. The detector 120 may be oriented such that its Y-axis is parallel to the scan axis. For this reason, the Y-axis may also be referred to as the axial dimension of the detector 120, and the X-axis may be referred to as the trans-axial dimension, or lateral dimension, of the device 120. The X-axis is perpendicular to a plane defined by the scan axis and the projection line, and the Y-axis is parallel to this same plane. Each pixel is assigned a discrete X-coordinate ("X") along the X-axis and a discrete Y-coordinate ("Y") along the Y-axis. A smaller number of pixels are shown in the figure for the sake of visual clarity. The detector may be centered on the projection line to enable full-fan imaging of the target object, may be offset from the projection line to enable half-fan imaging of the target object, or may be movable with respect to the projection line to allow both full-fan and half-fan imaging of target objects.

Figure 2:
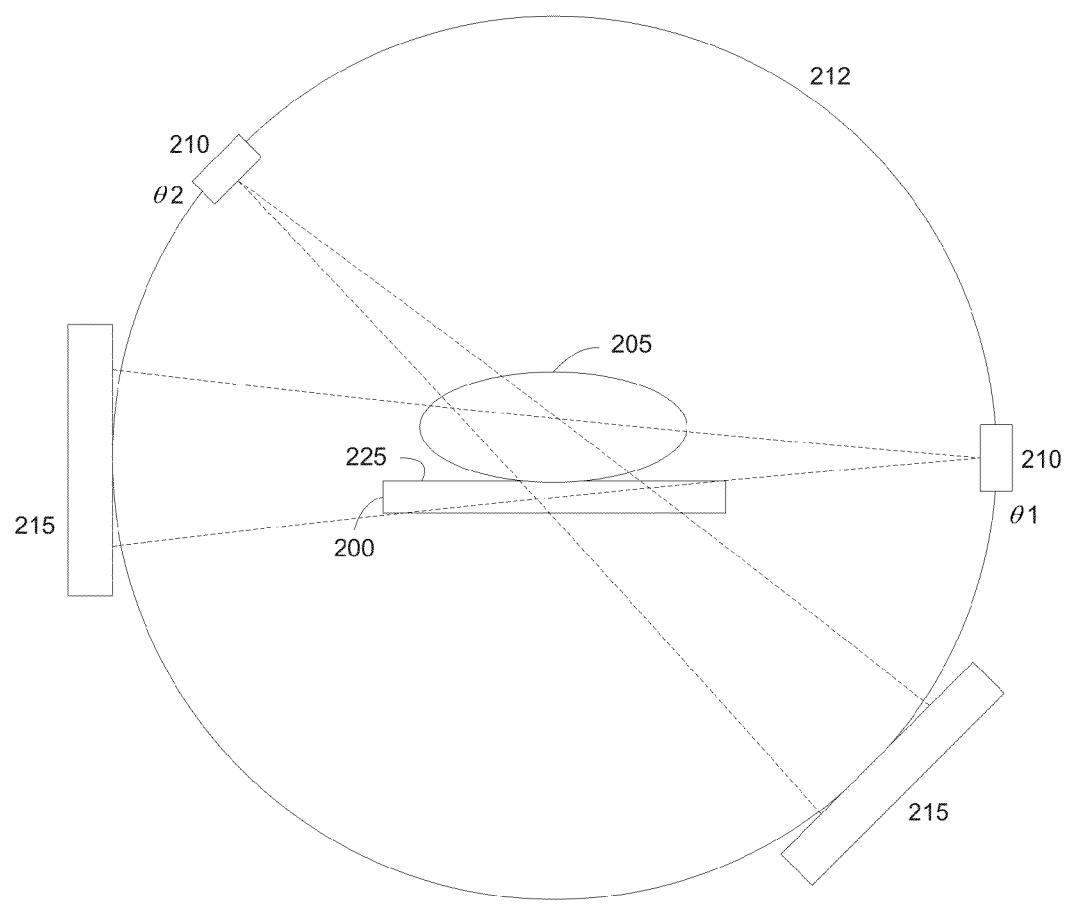
FIG. 2 is an example configuration of a table with respect to a target object on the table, a radiation source, and a detector, for two selected projection angles as provided by rotation of the gantry about the target object along a circular trajectory.

FIG. 2 is an example configuration of a table 200 with respect to a target object 205 on the table 200 (generally a patient), a radiation source 210, and a detector 215, for two selected projection angles as provided by rotation of the gantry about the target object along a circular trajectory 220, in accordance with at least some embodiments of the present disclosure. In this example, the x-y plane is defined as the plane of the paper. The z axis extends out from the paper. While the radiation source 210 may be rotated 360°, and projection data may be generated for every 1°, certain projection data at selected projection angles, such as $\theta 1$ and $\theta 2$ shown in FIG. 2, may be analyzed and processed differently. For instance, in scatter estimation models, such as the kernel models mentioned in the Background section above, the estimated scatter may be less accurate for certain projection angles, such as, without limitation, in the lateral direction (such as $\theta 1$), near approximately 45 degrees (not shown), near approximately 135 degrees (such as $\theta 2$). Subsequent paragraphs will further detail how the projection data at such angles of interest may be processed.

Figure 3:
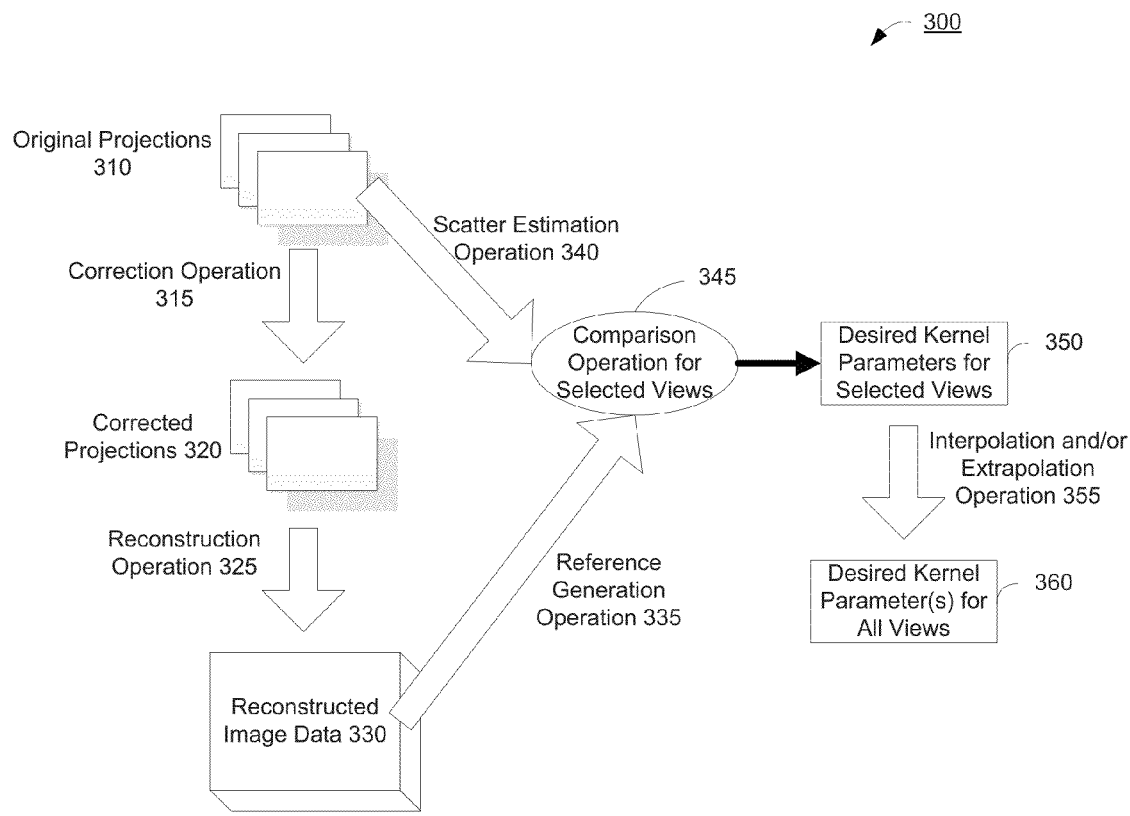
FIG. 3 is an example process flow for improving scatter estimates.

FIG. 3 is an example process flow for improving scatter estimates, in accordance with at least some embodiments of the present disclosure. An imaging system, such as the imaging system 100 of FIG. 1, generates a set of original projections 310. The original projections 310 may then be processed by one or more computing devices 170 also shown in FIG. 1.

In a first data processing path, the original projections 310 may be corrected in a correction operation 315 to generate corrected projections 320. Some example corrections may include, without limitation, scatter corrections. The corrected projections 320 are then further processed in a reconstruction operation 325 to generate reconstructed image data 330. Based on the reconstructed image data 330, reference scatter data are generated in a reference generation operation 335. In one implementation, the reference generation operation 335 may include additional operations such as, without limitation, converting the reconstructed image data 330, which for example could be in the Hounsfield Units (HUs) representation, to a 3D map of various materials and densities resembling the target object being imaged (e.g., bone structures, certain organs, etc.), modeling the imaging components of the imaging system 100 of FIG. 1 (e.g., the operation settings of the radiation source 110 and the detector 120, and/or beam filtration and modulator and anti-scatter grid (not shown), so that the imaging geometry and x-ray energy spectrum, for instance, of the imaging system 100 used to generate the original projections 310 may be considered to perform Monte Carlo simulations), and performing Monte Carlo simulations on a selected subset of the pixel detectors of the detector 120 (e.g., selected rows of the pixel detectors) and/or projection views at projection angles that may be known to yield undesirable scatter estimates, such as, without limitation, $\theta 1$ and $\theta 2$ to generate the reference scatter data. In other words, in one implementation, the aforementioned 3D map and/or the modeled imaging component information may be input to the Monte Carlo simulations. Alternatively, instead of performing Monte Carlo simulations, deterministic methods, such as, without limitation, solving deterministic particle transport equations such as the Boltzmann equation may be used to generate the reference scatter data. Similar to the Monte Carlo simulations, the aforementioned 3D map and/or the modeled imaging component information may also be input to solving the deterministic particle transport equations. In yet another alternative embodiment, scatter measuring techniques, such as, without limitation, the beam blocker method, modulation method, slit scan method, and collimator shadowing technique may be utilized to obtain the reference scatter data. In one implementation of the collimator shadowing technique, a portion of the detector 120, typically in one or more of its edges, may be blocked from a primary signal by the fan blades 130 or additional such devices.

Although the Monte Carlo simulations and the deterministic methods described above are performed based on the reconstructed image data 330, such scatter simulations and calculations may use data from a prior scan or imaging, such as a planning CT, to avoid the need of two-pass reconstruction operations.

In a second data processing path, a scatter estimation operation 340 using any of the kernel models mentioned in the Background section above is performed based on the original projections 310 to generate estimated scatter data. Then, the estimated scatter data from the second data processing path and the reference scatter data from the first data processing path are compared in a comparison operation 345. The estimated scatter data may also be used in the correction operation 315. In one implementation, the comparison operation 345 may include the following:

Suppose $S1(i,j)$ corresponds to the estimated scatter data, and $S2(i,j)$ corresponds to the reference scatter data, both at pixel detector location $(i,j)$ for a particular projection angle.

Define an example goal function, such as a root means square error, as:

$$g = \frac{\sqrt{\sum_i \sum_j \left(\frac{S1(i,j) - S2(i,j)}{S2(i,j)}\right)^2}}{\sum_i \sum_j 1}$$

where the summation i and j are done over a region of interest on the detector. The region of interest may correspond to the entire or just a partial area of the detector.

Identify kernel parameters of interest, for example, the kernel parameters having a large impact on resultant scatter estimates, such as A in symmetric or $\gamma$ and A in asymmetric kernel models or the weighting factor that combines different kernels in hybrid kernel models.

Find optimal kernel parameters of interest.

Using the kernel parameters $\gamma$ and A as an illustration, since the estimated scatter data S1 is a function of $\gamma$ and A, and the goal function g is also a function of $\gamma$ and A, the optimal $\gamma$ and A that minimizes g may be obtained by solving the optimization problem, $$\min_{\gamma, A} g(\gamma, A)$$

It is possible to choose other parameters as the parameters of interest. Specifically, in addition to object scatter related parameters, parameters of interest may include parameters that related to anti-scatter grid, detector scatter, and any parameters employed by scatter kernel superposition methods.

Once the comparison operation 345 outputs desired kernel parameters for selected projection views 350, desired kernel parameters for all projection views 360 are generated by performing an interpolation and/or extrapolation operation 355. To illustrate, suppose Am is the optimal A for the m-th view and An for the n-th view, for any view o in between, a linear interpolation operation may include Ao=Am+(An−Am)/(n−m)*(o−m). Similarly, the interpolation and/or extrapolation operation 355 may be applied to other kernel parameters, such as $\gamma$. Alternatively, the linear interpolation operation may be performed based on angular distances, with the consideration of angular wrap-around at 360 degrees, such as:

Ao=Am+(An−Am)/angle_distance_btw_n_and_m*angle_distance_btw_o_and_m

There are many ways of performing the interpolation and/or extrapolation operation 355. Some examples include, without limitation, non-linear interpolation approaches. Parameters from any number of optimized projection views can be used in the interpolation operation 355. For example, an operation employing a second order polynomial may require three optimized projections at once. A cubic spline interpolation may require four optimized projections each time. The view number and projection angle at the end of a scan may need to be taken into account in calculations. For example, when the scan is not 360 degrees, extrapolation operation may be needed in addition to interpolation.

In one embodiment, with the desired kernel parameters for all projection views, the kernels having such kernel parameters are applied to the original projections 310 to obtain an improved set of corrected projections 320, from which the improved reconstructed image data 330 are generated.

FIGS. 4-7 are line profiles from the central rows of representative views of an elliptical water cylinder before and after applying optimal kernel parameters, in accordance with at least some embodiments of the present disclosure. FIGS. 8-11 are line profiles from the central rows of another set of representative views of an elliptical water cylinder before and after applying interpolated kernel parameters, in accordance with at least some embodiments of the present disclosure. The angular position of the radiation source and detector with respect to the target object is also shown. The black lines shown in these figures correspond to "total signals" (i.e., the combination of primary signals and scatter signals). The thick gray lines correspond to the reference scatter data, and the thin gray lines correspond to the estimated scatter data. The x-axis of the plots in FIGS. 4-11 corresponds to the column position of signal samples in units of detector pixels. The y-axis corresponds to the detector signal in digital units, such as Analog to Digital Units (ADUs).

Figure 4:
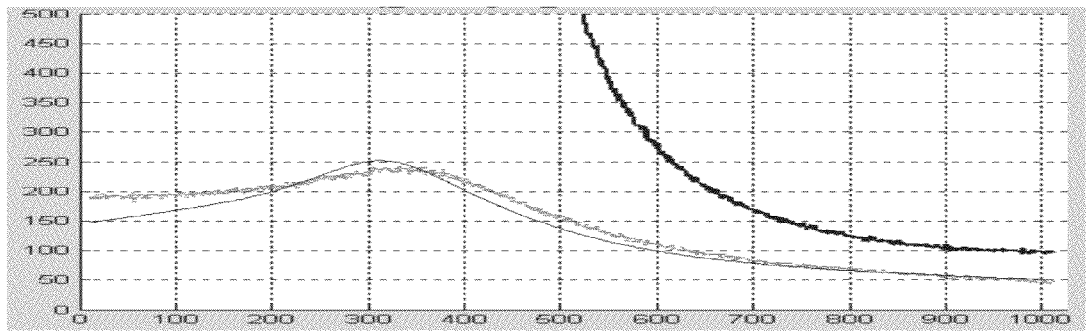
FIGS. 4-7 are representative views of an elliptical water cylinder using optimal kernel parameters.
Figure 4:
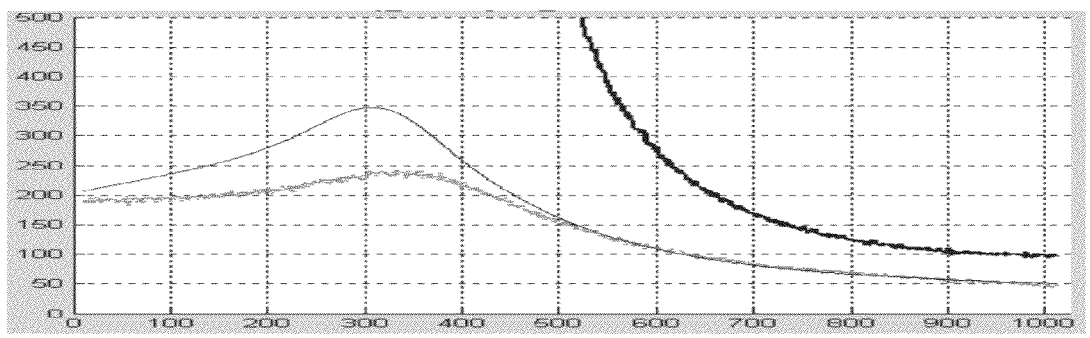
Figure 4:
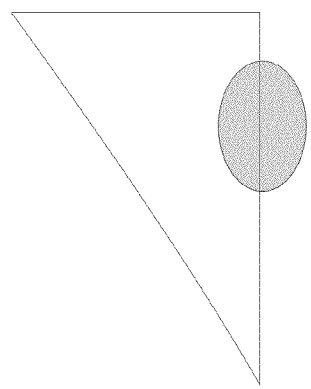
Figure 5:
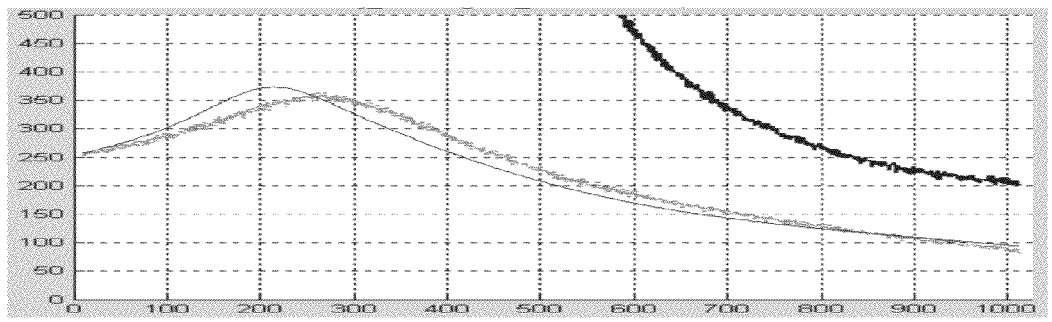
Figure 5:
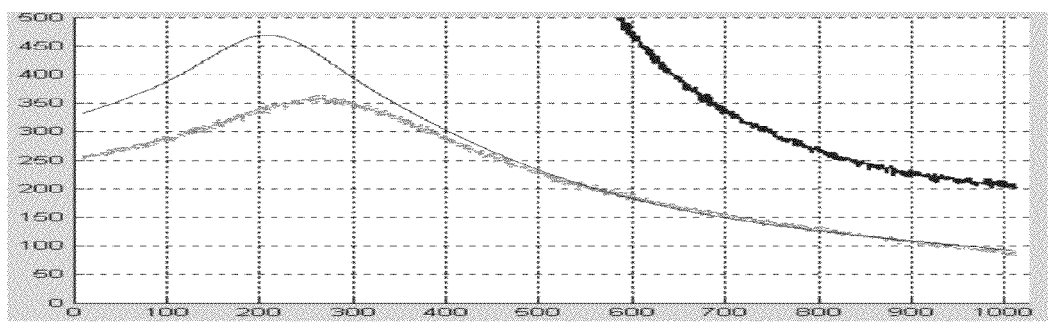
Figure 5:
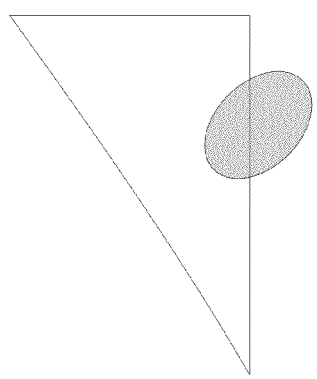
Figure 6:
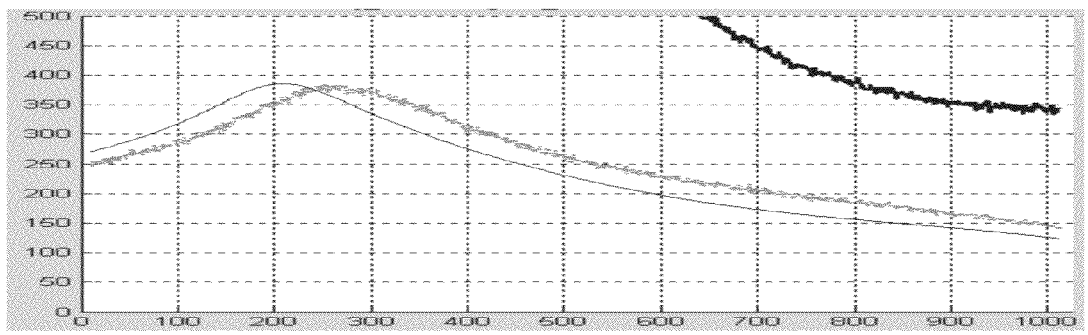
Figure 6:
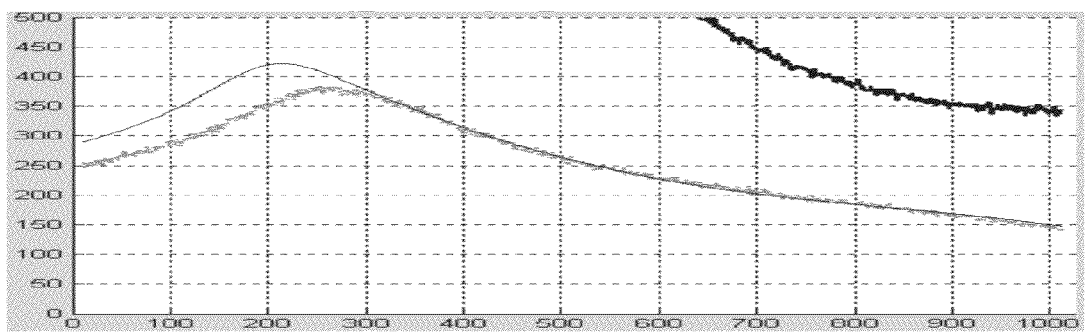
Figure 6:
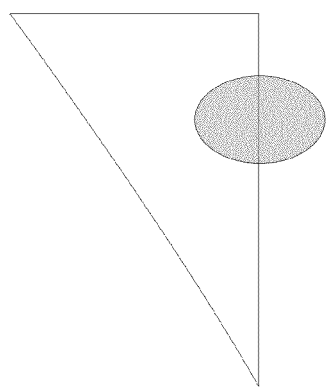
Figure 7:
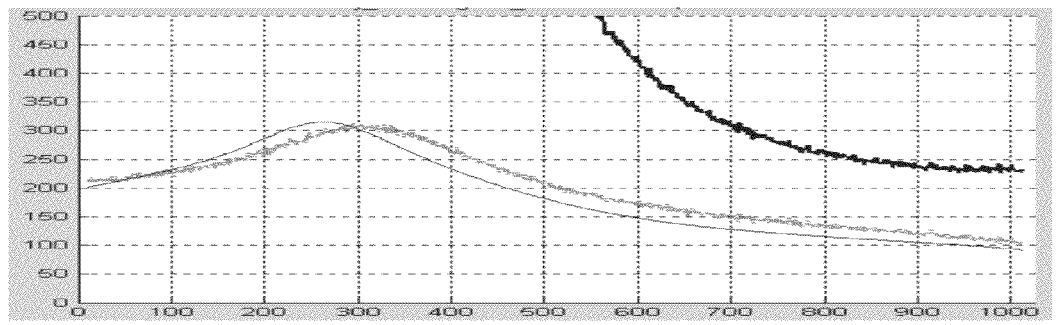
Figure 7:
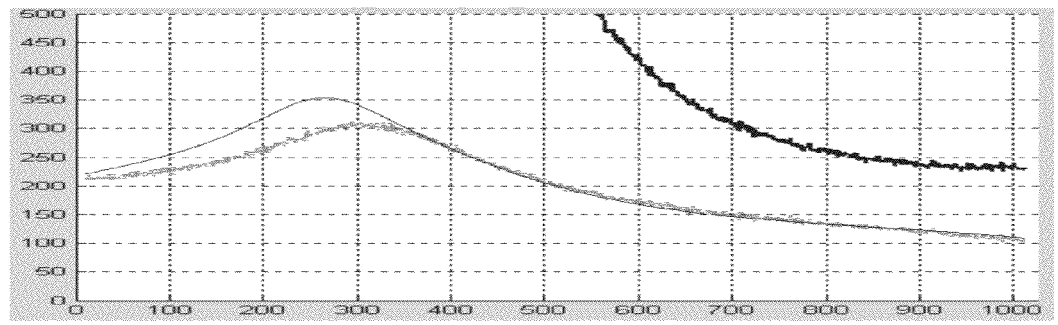
Figure 7:
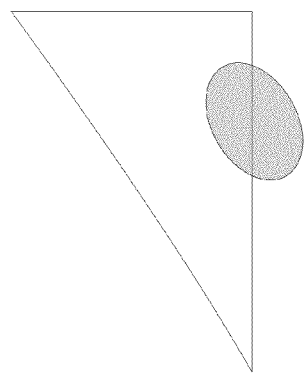
Figure 8:
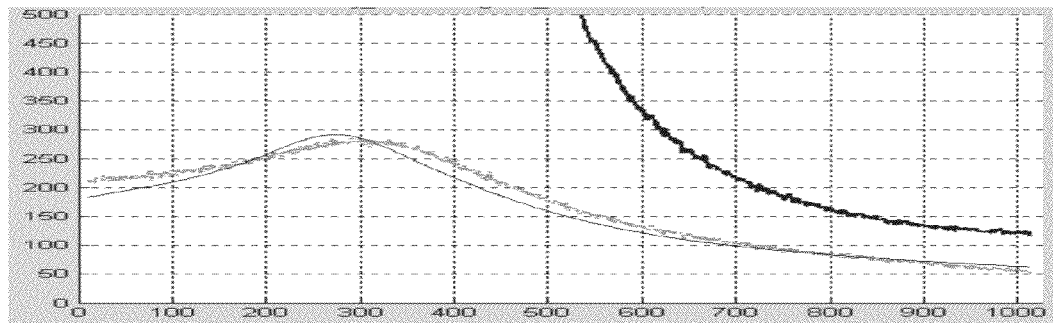
FIGS. 8-11 are representative views of an elliptical water cylinder using interpolated kernel parameters, all arranged in accordance with at least some embodiments of the present disclosure.
Figure 8:
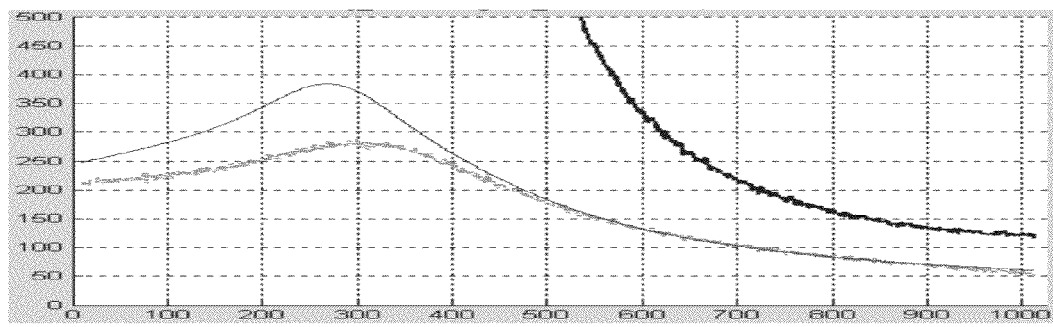
Figure 8:
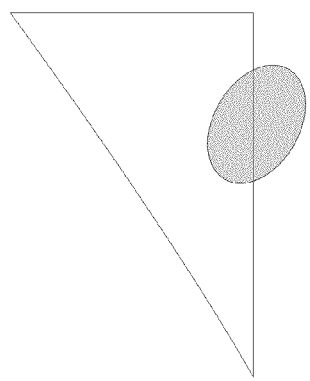
Figure 9:
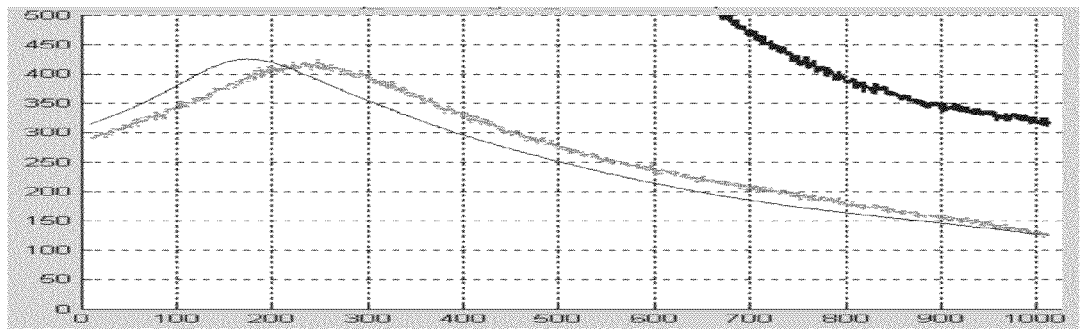
Figure 9:
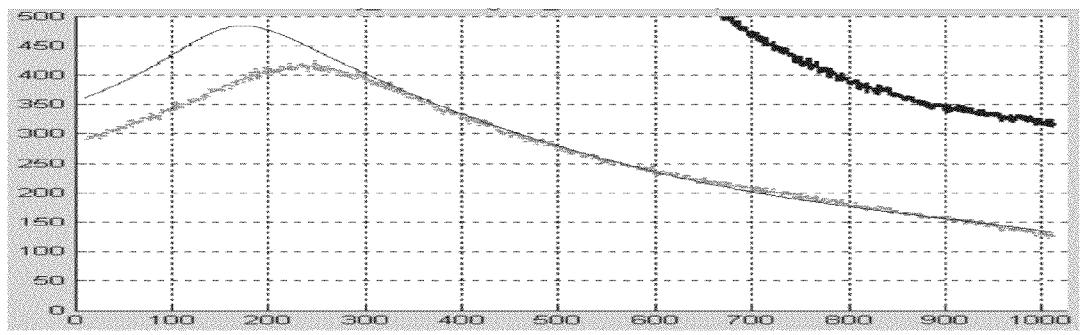
Figure 9:
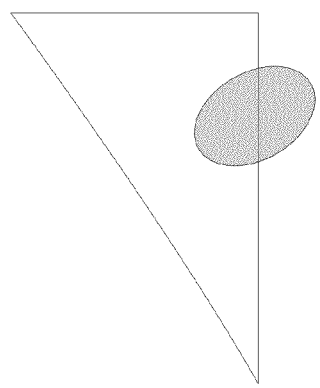
Figure 10:
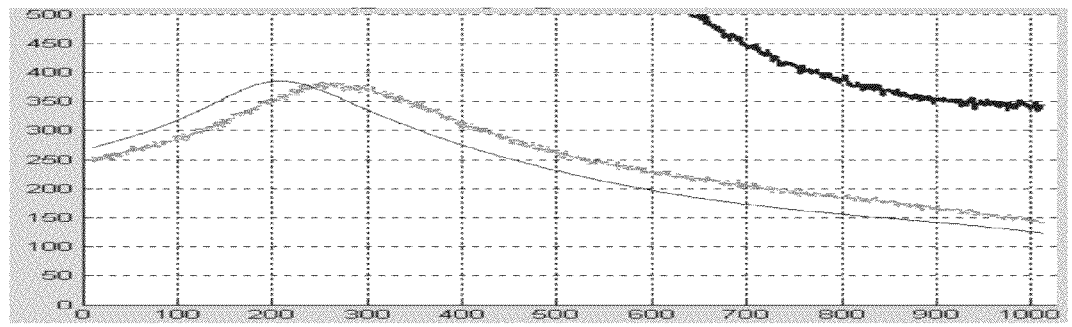
Figure 10:
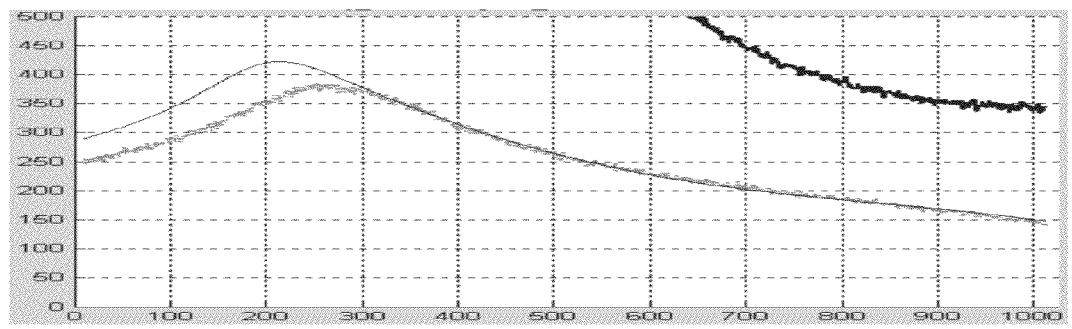
Figure 10:
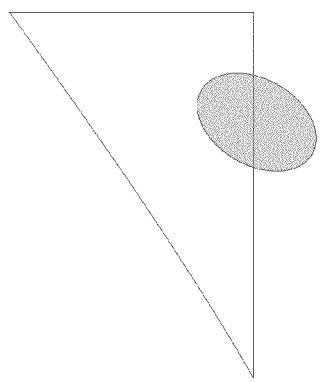
Figure 11:
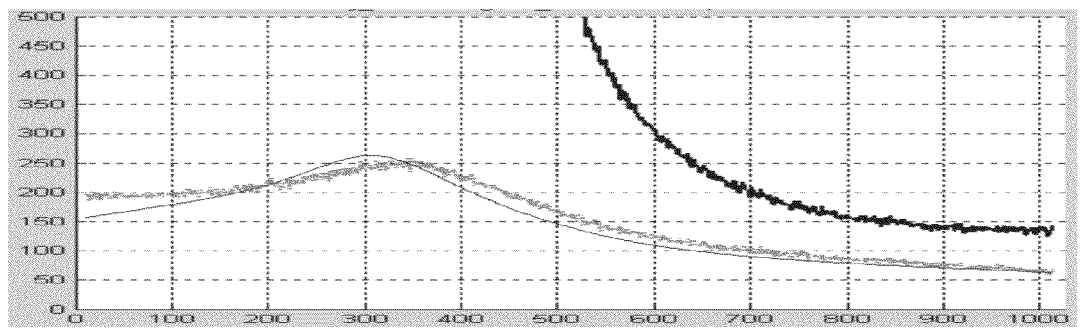
Figure 11:
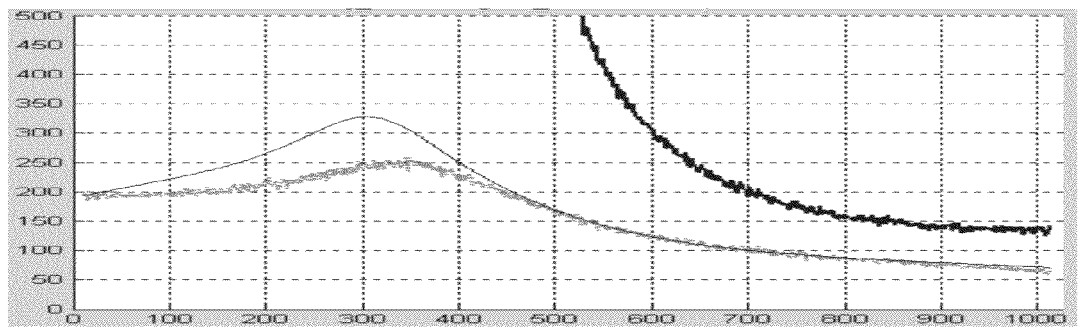
Figure 11:
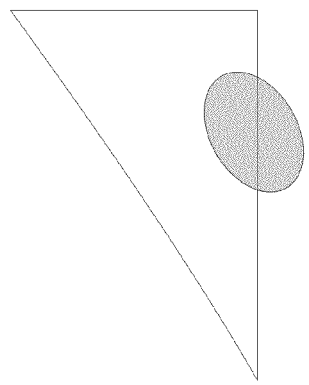

In FIG. 4, the before plot is generated with $\gamma$=0.16 and A=1, and the after plot is generated with $\gamma$=0.204 and A=1.28. In FIG. 5, the before plot is generated with $\gamma$=0.16 and A=1, and the after plot is generated with $\gamma$=0.187 and A=1.24. In FIG. 6, the before plot is generated with $\gamma$=0.16 and A=1, and the after plot is generated with $\gamma$=0.127 and A=1.13. In FIG. 7, the before plot is generated with $\gamma$=0.16 and A=1, and the after plot is generated with $\gamma$=0.154 and A=1.13. In FIG. 8, the before plot is generated with $\gamma$=0.16 and A=1, and the after plot is generated with $\gamma$=0.196 and A=1.26. In FIG. 9, the before plot is generated with $\gamma$=0.16 and A=1, and the after plot is generated with γ=0.157 and A=1.18. In FIG. 10, the before plot is generated with γ=0.16 and A=1, and the after plot is generated with γ=0.141 and A=1.13. In FIG. 11, the before plot is generated with γ=0.16 and A=1, and the after plot is generated with γ=0.179 and A=1.21. In all these plots, the estimated scatter matches the reference scatter better after using the optimized or interpolated scatter parameters, especially in the region where the primary signal is low where a small error in scatter could correspond to a non-trivial error in the primary signal. The optimal parameters in FIGS. 4-7 exhibit small ranges of variations that are relatively smooth as a function of projection angles. Thus, interpolating these optimal parameters for the other projection angles may yield desirable results, as is evident in FIGS. 8-11.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense.

We claim:

1. A method for an imaging system to estimate scatter associated with a target object, comprising:
generating, by the imaging system, a set of original projections associated with the target object;
generating, by the imaging system, a set of reference scatter data associated with the target object at one or more selected projection angles;
generating, by the imaging system, a first set of estimated scatter data associated with the target object by applying one or more kernels with first values for one or more kernel parameters to a first subset of projections out of the set of original projections at the one or more selected projection angles;
adjusting, by the imaging system, the first values for the one or more kernel parameters of the one or more kernels that reduce a difference between the set of reference scatter data and the first set of estimated scatter data;
interpolating, by the imaging system, the adjusted first values for remaining projections out of the set of original projections to generate second values for the one or more kernel parameters; and
generating, by the imaging system, a second set of estimated scatter data associated with the target object by applying the one or more kernels with the adjusted first values and the second values for the one or more kernel parameters.

2. The method of claim 1, wherein the generating a set of reference scatter data comprises:
generating, by the imaging system, reconstructed image data of the target object based on a set of corrected projections, wherein the set of corrected projections are derived from the set of original projections;
converting, by the imaging system, the reconstructed image data to a three-dimensional (3D) map; and
based on any combination of imaging geometry and imaging components of the imaging system, the reconstructed image data, and the 3D map, performing operations, by the imaging system, at the one or more selected projection angles.

3. The method of claim 2, wherein the performing operations includes performing Monte Carlo simulations.

4. The method of claim 2, wherein the performing operations includes solving equations relating to a deterministic method.

5. The method of claim 2, wherein the generating reconstructed image data of the target object is based on a prior imaging associated with the target object.

6. The method of claim 1, wherein the generating a set of reference scatter data is associated with a selected subset of pixel detectors of the imaging components.

7. The method of claim 1, wherein the generating a set of reference scatter data comprises measuring scatter during a scan at the one or more selected projection angles.

8. The method of claim 1, wherein the adjusting the first values for one or more kernel parameters comprises:
defining a goal function of the one or more kernel parameters that involves the difference between the set of reference scatter data and the first set of estimated scatter data; and
determining the adjusted first values for the one or more kernel parameters that minimize the goal function.

9. The method of claim 1, wherein the generating a set of reference scatter data is performed in a first data processing path, the generating a first set of estimated scatter data is performed in a second data processing path, and the first data processing path and the second data processing path are independent of one another.

10. The method of claim 1, further comprising selecting the one or more selected projection angles wherein scatter estimates generated at the one or more selected projection angles are known to be undesirable.

11. An imaging system configured to estimate scatter associated with a target object, comprising:
a radiation source;
a detector;
a controller; and
a computing device coupled to the controller, wherein
the radiation source and the detector are configured to generate a set of original projections associated with the target object, and
the computing device is configured to
generate a set of reference scatter data associated with the target object at one or more selected projection angles,
generate a first set of estimated scatter data associated with the target object by applying one or more kernels with first values for one or more kernel parameters to a first subset of projections out of the set of original projections at the one or more selected projection angles, adjust the first values for one or more kernel parameters of the one or more kernels that reduce a difference between the set of reference scatter data and the first set of estimated scatter data, interpolate the adjusted first values for remaining projections out of the set of original projections to generate second values for the one or more kernel parameters, and generate a second set of estimated scatter data associated with the target object by applying the one or more kernels with the adjusted first values and the second values for the one or more kernel parameters.

12. The imaging system of claim 11, wherein the computing device is configured to generate the set of reference scatter data by:

generating reconstructed image data of the target object based on a set of corrected projections, wherein the set of corrected projections are derived from the set of original projections;

converting the reconstructed image data to a three-dimensional (3D) map; and based on any combination of imaging geometry of the imaging system, first operation settings of the radiation source, second operation settings of the detector, the reconstructed image data, and the 3D map, performing operations at the one or more selected projection angles.

13. The imaging system of claim 12, wherein the computing device is configured to perform Monte Carlo simulations.

14. The imaging system of claim 12, wherein the computing device is configured to solve equations relating to a deterministic method.

15. The imaging system of claim 12, wherein the computing device is configured to generate the reconstructed image data of the target object based on a prior imaging associated with the target object.

16. The imaging system of claim 11, wherein the computing device is configured to perform the operations associated with a selected subset of pixel detectors of the detector.

17. The imaging system of claim 11, wherein the computing device is configured to generate the set of reference scatter data by measuring scatter during a scan at the one or more selected projection angles.

18. The imaging system of claim 11, wherein the computing device is configured to adjust the first values for one or more kernel parameters by:

defining a goal function of the one or more kernel parameters that involves the difference between the set of reference scatter data and the first set of estimated scatter data; and determining the adjusted first values for the one or more kernel parameters that minimize the goal function.

19. The imaging system of claim 11, wherein the computing device is configured to generate the set of reference scatter data in a first data processing path and generate the first set of estimated scatter data in a second data processing path, wherein the first data processing path and the second data processing path are independent of one another.

20. The imaging system of claim 11, wherein the computing device is further configured to select the one or more selected projection angles wherein scatter estimates generated at the one or more selected projection angles are known to be undesirable.

* * * * *